(12) United States Patent
Wilsey et al.

(10) Patent No.: US 6,541,216 B1
(45) Date of Patent: Apr. 1, 2003

(54) AMPEROMETRIC BIOSENSOR TEST STRIP

(75) Inventors: Christopher Douglas Wilsey, Carmel, IN (US); David W. Burke, Carmel, IN (US)

(73) Assignee: Roche Diagnostics Corporation, Indianapolis, IN (US)

( * ) Notice: Subject to any disclaimer, the term of this patent is extended or adjusted under 35 U.S.C. 154(b) by 0 days.

(21) Appl. No.: 09/469,899

(22) Filed: Dec. 22, 1999

(51) Int. Cl.$^7$ .............. C12Q 1/32; C12Q 1/44; C12Q 1/34; C12Q 1/48; C12M 1/00

(52) U.S. Cl. .............. 435/26; 435/19; 435/18; 435/283.1; 435/287.1; 435/817; 435/15

(58) Field of Search .............. 435/26, 19, 18, 435/15, 283.1, 287.1, 817

(56) References Cited

U.S. PATENT DOCUMENTS

| | | | |
|---|---|---|---|
| 3,880,590 A | 4/1975 | Ogawa et al. | 23/253 TP |
| 3,964,870 A | 6/1976 | Tiedemann et al. | 23/253 TP |
| 3,964,974 A | 6/1976 | Banauch et al. | 195/103.5 C |
| 4,097,240 A | 6/1978 | Hirsch | 23/253 TP |
| 4,147,514 A | 4/1979 | Magers et al. | 23/230 B |
| 4,184,850 A | 1/1980 | Habenstein | 23/230 B |
| 4,193,766 A | 3/1980 | Daunora et al. | 23/230 R |
| 4,254,222 A | 3/1981 | Owen | 435/26 |
| 4,351,899 A | 9/1982 | Owen | 435/26 |
| 4,397,956 A | 8/1983 | Maggio | 436/34 |
| 4,405,721 A | 9/1983 | Kohl | 436/128 |
| 4,440,724 A | 4/1984 | Tabb et al. | 422/56 |
| 4,517,301 A | 5/1985 | Greene | 436/14 |
| 4,529,704 A | 7/1985 | Trimmer et al. | 436/14 |
| 4,758,323 A | 7/1988 | Davis et al. | 204/403 |
| 4,803,158 A | 2/1989 | Shigeta et al. | 435/25 |
| 4,970,172 A | 11/1990 | Kundu | 436/130 |
| 5,028,542 A | 7/1991 | Kennamer et al. | 436/14 |
| 5,071,769 A | 12/1991 | Kundu et al. | 436/128 |
| 5,190,863 A | 3/1993 | Magers | 435/25 |
| 5,288,636 A | 2/1994 | Pollmann et al. | 435/288 |
| 5,326,697 A | 7/1994 | Magers | 435/25 |
| 5,510,245 A | 4/1996 | Magers | 435/26 |
| 5,618,686 A | 4/1997 | Kojima et al. | 435/26 |
| 5,633,143 A | 5/1997 | Ueda et al. | 435/26 |
| 5,762,770 A | 6/1998 | Pritchard et al. | 204/403 |
| 5,801,059 A | 9/1998 | Smith et al. | 436/128 |
| 5,997,817 A * | 12/1999 | Crismore et al. | 422/58 |

FOREIGN PATENT DOCUMENTS

| | | | |
|---|---|---|---|
| EP | 0 184 895 B1 | 6/1988 | .......... C12M/1/40 |
| EP | 0 230 786 B1 | 9/1991 | .......... C12M/1/40 |
| EP | 0 127 958 B2 | 4/1996 | .......... G01N/33/48 |
| WO | WO 9919507 | 4/1999 | |
| WO | WO 99/19507 | 4/1999 | .......... C12Q/1/00 |
| WO | 200146457 | * 6/2001 | |

OTHER PUBLICATIONS

Selim Baruh, et al., "Diabetic Ketoacidosis and Coma," Symposium on Acute Medical Illness, Medical Clinics of North America, 65:117–132 (1981).

Batchelor, et al., "Amperometric Assay For The Ketone Body D–3–Hydroxybutyrate," Analytica Chimica Acta, 221:289–294 (1989).

(List continued on next page.)

*Primary Examiner*—Louise N. Leary
(74) *Attorney, Agent, or Firm*—Jill L. Woodburn

(57) ABSTRACT

A reagent and method for determining the levels of 3-hydroxybutyric acid in a sample are provided. The reagent comprises a ferricyanide salt, a catalytic amount of a first enzyme operative to catalyze the oxidation of 3-hydroxybutyric acid in the sample, a cofactor corresponding to said first enzyme, and a catalytic amount of a second enzyme operative to catalyze the oxidization of the cofactor and the reduction of the ferricyanide. The reagent is incorporated into a test strip that generates an electrical output signal indicative of the level of 3-hydroxybutyric acid when the reagent is contacted with a sample.

30 Claims, 3 Drawing Sheets

OTHER PUBLICATIONS

Foster, et al., "The Metabolic Derangements and Treatment of Diabetic Ketoacidosis," The New England Journal of Medicine, 309: 159–168 (1983).

Rochelle Marie Hanley, M.D., "'Diabetic' emergencies—They happen with or without diabetes," Postgraduate Medicine, 88:90–99 (1990).

Hansen, et al., "Direct Assays of Lactate, Pyruvate, Beta–Hydroxybutyrate, and Aceotoacetate with a Centrifugal Analyzer," Clinical Chemistry 24:475–479 (1978)37.

Harano, et al., "Sensitive and simplified method for the differential determination of serum levels of ketone bodies," Clinica Chimica Acta. 134:327–336 (1983).

McMurray, et al., "Automated Kinetic Method for D–3–Hydroxybutyrate in Plasma or Serum," Clinical Chemistry 30:421–425 (1984).

Persson, B., "Determination of Plasma Acetoacetate and D–Beta–Hydroxybutyrate in New–born Infants by an Enzymatic Fluorometric Micro–method," Scand. J. clin. Lab. Invest. 25:9–18 (1969).

Ruell, et al., "Enzymatic measurement of 3–hydroxybutyrate in extracts of blood without neutralization," Ann Clin. Biochem. 28:183–184 (1991).

Williamson, et al., "Enzymic Determination of D(-)-Beta–Hydroxybutyric Acid and Acetoacetic Acid in Blood," Biochem. J. 82:90–95 (1962).

Zivin, et al., "An Automated Colorimetric Method for the Measurement of 3–Hydroxybutyrate Concentration," Analytical Biochemistry, 52:456–461 (1973).

Abbott Laboratories, MediSense Products, Assessing metabolic status with beta–hydroxybutrate—Precision(R), Xtra(R), Apimall—The Health Channel (1999).

Boehringer Mannheim Diagnostics, "SingleVial Alpha–H-BDH UV Method Catalog No. 124800—For The Quantitative Determination of Alpha–Hydroxybutyrate Dehydrogenase in Serum or Plasma".

ICN Biochemicals, "D–3–Hydroxybutyrate Dehydrogenase from Pseudomonas sp." 301 HBD, Jun. 1, 1993.

Kyoto Daiichi Kagaku Co., Ltd., "For Real–Time Monitoring of Blood Ketone Body—System for Blood Ketone Body (3–Hydroxybutyric Acid) Measurement—Test Strip for Ketone Body Measurement: Instrument for Ketofilm—Ketofilm/KETO Meter".

Toyobo Co., Ltd., "Toyobo Enzymes (Diagnostic Reagent Grade) D–3–Hydroxybutyrate Dehydrogenase from Pseudomonas sp.".

* cited by examiner

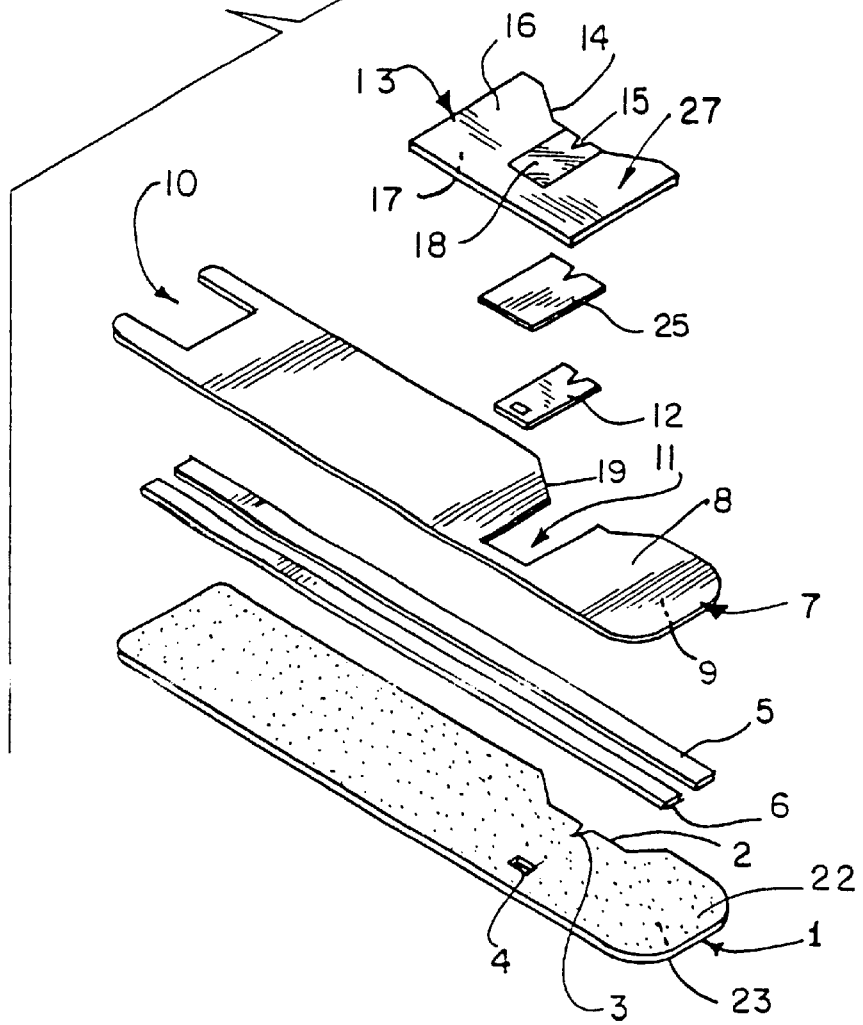

AMPEROMETRIC BIOSENSOR TEST STRIP

FIELD OF THE INVENTION

This invention relates to the determination of the concentration of analytes in fluids and more specifically to an amperometric biosensor for use in such determination. Most particularly, this invention relates to an amperometric biosensor used in the determination of 3-hydroxybutyric acid levels in fluids.

BACKGROUND OF THE INVENTION 3-hydroxybutyric acid (hereinafter "3-HBA") is produced by incomplete fatty acid metabolism in the liver under conditions involving the impaired utilization or inadequate supply of carbohydrates. Whenever increased amounts of fats are metabolized, such as when the carbohydrate intake is restricted, the concentration of ketone bodies such as 3-HBA, acetone, and acetoacetic acid can increase. If ketone bodies are present in the blood in an excessive amount, the condition is termed ketosis.

Diabetes mellitus is a disorder associated with ketosis. Diabetes mellitus is a disorder of glucose metabolism. In insulin-deficient diabetes, glucose metabolism is sufficiently impaired such that fatty acids are utilized to meet the energy requirements of the body. If excessive amounts of fatty acids are metabolized, ketone bodies accumulate in the blood, i.e., ketosis, and are excreted in urine, i.e. ketonuria. In addition, ketone bodies are excreted from the body in combination with normal basic ions, thereby reducing the carbon dioxide combining power of the body and causing systemic acidosis, i.e. increased acidity of the blood. The term ketoacidosis designates the combined ketosis and acidosis conditions associated with diabetes. At elevated levels, 3-HBA is diagnostic of ketoacidosis.

Detecting ketoacidosis in a patient with diabetes mellitus is beneficial in that it often indicates the necessity of a change in insulin dosage or other management procedures. One approach to determine the presence or concentration of ketone bodies in a sample has been to subject the sample to a colorimetric assay. For example, it is well known to determine the presence or concentration of ketone bodies by contacting a liquid sample with an indicator reagent composition that undergoes a color transition upon contact with the sample. See for example, U.S. Pat. Nos. 4,803,158; 5,326,697; 5,510,245; and 5,190,863.

Amperometric assays for ketone bodies have also been used. See for example, PCT/US98/21815, filed Oct. 16, 1998, and Batchelor, et al., *Amperometric Assay for the Ketone Body Hydroxybutyrate*, Analytic Chimica Acta. 289–294 (1989). These assays utilize enzymes to catalyze the oxidation of 3-HBA, the oxidizable form of a cofactor, and an oxidant such as, for example, a quinone.

SUMMARY OF THE INVENTION

Biosensor and method of the present invention allows the user to test blood ketones in an amperometric meter that is also used to test for glucose. Biosensor test strip of this invention is compatible with commercially available amperometric glucose measuring sensors. The test strip comprises a reagent that is reactive with the sample in a manner effective to generate an electrical output signal indicative of the level of 3-hydroxybutyric acid (hereinafter "3-HBA") in the sample. The reagent comprises a ferricyanide salt, a catalytic amount of a first enzyme operative to catalyze the oxidation of 3-HBA in the sample, a mediator corresponding to said first enzyme, and a catalytic amount of a second enzyme operative to catalyze the electrochemical oxidation of a reduced form of the cofactor.

The test strip includes at least two electrically conducting tracks insulated from each other. Each of the tracks is adapted to be in electrical contact with the reagent. One of the tracks accepts electron transfer from the reagent, wherein the amount of the electron transfer is indicative of the level of 3-HBA in the sample.

A method is also provided for determining information indicative of the level of 3-HBA in a sample is provided, which is compatible with commercially available amperometric glucose measuring sensors. The method comprises reacting the sample with a reagent comprising a ferricyanide salt, a catalytic amount of a first enzyme operative to catalyze the oxidation of 3-HBA in the sample, a cofactor corresponding to said first enzyme, and a catalytic amount of a second enzyme to catalyze the electrochemical oxidation of a reduced form of the cofactor. The reagent generates an electrical output indicative of the level of 3-HBA in the sample. The electrical output is then measured and the level of 3-HBA in the sample is determined using information comprising the measured electrical output.

Still further, in accordance with the present invention a method for determining information indicative of the level of 3-HBA in a sample is provided. The method comprises the steps of providing a sensor including a working and counter electrodes and a reagent in communication with the electrodes, the reagent comprising a ferricyanide salt, a catalytic amount of a first enzyme operative to catalyze the oxidation of 3-HBA in the fluid sample, a cofactor corresponding to said first enzyme, and a catalytic amount of a second enzyme to catalyze the electrochemical oxidation of a reduced form of the cofactor. The reagent is contacted with the fluid sample and a direct potential difference is applied between the electrodes that is sufficient to generate an electrical output from the reagent indicative of the level of 3-HBA in the fluid sample.

Additional features and advantages of the invention will become apparent to those skilled in the art upon consideration of the following detailed description and preferred embodiments exemplifying the best mode of carrying out the invention as presently perceived.

BRIEF DESCRIPTION OF THE DRAWINGS

FIG. 1 is an exploded perspective view of a test strip in accordance with the present invention showing the strip including a first insulating substrate, electrically conductive tracks formed to lie on first insulating substrate, a test reagent aligned with the tracks, a second insulating substrate, a hydrophilic coating, and a roof;

FIG. 2 is perspective view of the test strip of FIG. 1;

DETAILED DESCRIPTION OF THE INVENTION

Figure 3:
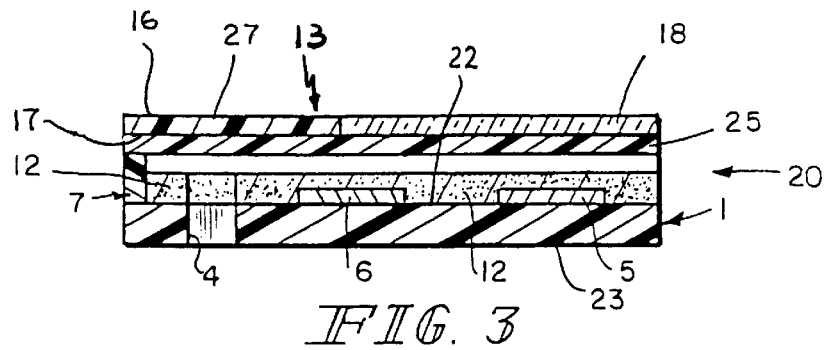
FIG. 3 is a cross-sectional view taken along lines 28—28 of FIG. 2 showing the relative positioning of the electrodes, reagent, and hydrophilic film between the first and second insulating substrates.

The field of electrochemistry is based on the phenomenon that many metals, metal ions, and conjugated molecules easily accept and/or release electrons. Compounds have a standard potential, which is the energy level at which the compound is equally likely to release or accept elections. Whether a compound is oxidized or reduced is dependent upon whether the potential applied to that compound is greater or less than its standard potential. The present invention relies upon an electrochemical technique known as amperometry, which involves applying a potential and collecting the moving electrons as current.

It has been discovered that hexacyanoferrate (III) salts may be used as mediators and incorporated into an amperometric biosensor test strip that generates an electrical output signal indicative of the level of 3-HBA in a sample. The use of hexacyanoferrate (III) salts as mediators in a test strip for 3-HBA is advantageous, because the corresponding test strip is compatible with existing amperometric glucose meters, allowing testing of ketones and glucose in one meter. The term mediator as used in the specification and claims comprises oxidants that are capable of undergoing an electrochemical, reversible, oxidation-reduction reaction. The oxidized form of the mediator must be capable of receiving at least one electron from a reaction involving an enzyme, analyte (or cofactor produced from analyte reaction) and the oxidized form of the mediator.

These mediators can be used in the manufacture an amperometric biosensor test strip for an analyte such as 3-HBA, which generates an electrical output indicative of the level of 3-HBA in the applied sample. The test strip is formed to receive biological samples such as whole blood, serum, and plasma. The test strip includes a reagent that comprises a mediator, a catalytic amount of a first enzyme operative to catalyze the oxidation of 3-HBA in a sample, a cofactor corresponding to said first enzyme, and a catalytic amount of a second enzyme operative to catalyze the electrochemical oxidation of a reduced form of the cofactor.

The reagent composition is incorporated into a biosensor test strip apparatus that determines the level of 3-hydroxybutyric acid (hereinafter "3-HBA") in the sample. Without being bound by theory, it is believed that the reagent composition reacts with 3-HBA in a binary reaction scheme. The first reaction involves oxidation of substantially of the 3-HBA in the sample, and the second reaction involves the electrochemical oxidation of one or more reduced reaction products resulting from the first reaction. The electrochemical oxidation generates a current whose strength is indicative of the amount of 3-HBA in the blood sample. The reagent composition includes the mediator ferricyanide, the enzymes 3-hydroxybutyrate dehydrogenase and diaphorase (each catalyzing one of the reactions), and the cofactor NAD$^+$. Accordingly, the 3-hydroxybutyrate dehydrogenase and diaphorase react in sequence, as shown in the following reaction scheme, in an assay for the presence or concentration of 3-HBA in a sample.

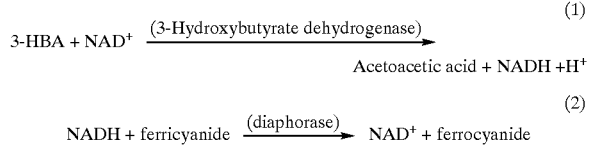

(1) 3-HBA + NAD$^+$ $\xrightarrow{\text{(3-Hydroxybutyrate dehydrogenase)}}$ Acetoacetic acid + NADH + H$^+$ (2) NADH + ferricyanide $\xrightarrow{\text{(diaphorase)}}$ NAD$^+$ + ferrocyanide Making use of the principle, when a sample containing the analyte 3-HBA is added to the reagent, the analyte is oxidized and the oxidized form of the cofactor is reduced. This cofactor then interacts with a second enzyme and the oxidized mediator is reduced. The reaction is allowed to reach a point where additional time is not necessary for the accurate determination of analyte concentration.

After the reactions are complete, a power source (e.g. a battery) applies a potential difference between a working and counter electrode. When the potential difference is applied, the amount of oxidized form of the mediator at the counter electrode and the potential difference must be sufficient to cause diffusion limited electro-oxidation of the reduced form of the mediator at the working electrode surface. A current measuring meter measures the diffusion limited current generated by the oxidation of the reduced form of the mediator at the working electrode surface to correlate the measured current to the concentration of 3-HBA in the sample.

Thus, the test strip and method utilizing the reagent of the present invention provide the user with a convenient and easy method for determining the levels of 3-HBA in the blood. The test strip and method essentially eliminate the disadvantages to the user having to purchase or use separate instrumentation for testing for blood glucose and for 3-HBA. The test strip apparatus is constructed similarly to the test strip described in U.S. Pat. No. 5,997,817 to Crismore et al., the disclosure of which is incorporated herein by reference. It is appreciated, however, that the test strip may be similar to the biosensors disclosed in U.S. Pat. No. 5,288,636 to Pollmann et al. and U.S. Pat. No. 5,762,770 to Pritchard et al., as well as any number of commercially available architectural environments for glucose measuring sensors without exceeding the scope of the present disclosure.

Referring specifically to FIGS. 1–2, the biosensor test strip of the present invention includes a first insulating substrate 1, a second insulating substrate 7, electrically conductive tracks 5, 6 situated between substrates 1, 7, a testing reagent 12, a generally hydrophilic film 25 in general alignment with testing reagent 12, and a roof 13 positioned over film 25. Reagent 12, as will be discussed hereafter, comprises the reagent composition of the present invention. In addition, test strip is produced from rolls of material. Thus, the selection of materials for the construction of the test strip necessitates the use of materials that are sufficiently flexible for roll processing, but which are still rigid enough to give a useful stiffness to the finished test strip.

First substrate 1 includes a first surface 22 that supports conductive tracks 5, 6 and an opposite second surface 23. See FIG. 1. First substrate 22 further includes an indentation 2, a notch 3, and a vent hole 4 extending between first and second surfaces 22, 23. Substrate 1 may be constructed from a wide variety of insulating materials. Non-limiting examples of insulating materials that provide desirable electrical and structural properties include vinyl polymers, polyimides, polyesters, and styrenics. The first insulating substrate 1 is 7 mil thick MELINEX 329 plastic, a polyester available from DuPont (3411 Silverside Road, PO Box 15391, Wilmington, Del. 19850).

As shown in FIG. 1, electrically conductive tracks 5 and 6 are laid down onto first surface 22 of first insulating substrate 1. Track 5 may be a working electrode and track 6 may b a counter electrode. Tracks 5, 6 are constructed from electrically-conductive materials. Specifically, track may be constructed of palladium, platinum, gold, carbon, and titanium. Track 6 may be constructed of palladium, platinum, gold, silver, silver containing alloys, nickel-chrome alloys, carbon, titanium, and copper.

Electrically conductive tracks 5 and 6 are deposited on an insulative backing, such as polyimide or polyester, to reduce the possibility of tearing the electrode material during handling and manufacturing of the test strip. An example of such conductive tracks is a palladium coating with a surface resistance of less than 5 ohms per square on the polyimide UPILEX from UBE INDUSTRIES, LTD., Japan, which is available pre-coated with gold, palladium or platinum from TECHNI-MET of Connecticut, USA.

Electrically conductive tracks 5 and 6 represent the electrodes of the biosensor test strip. These electrodes must be sufficiently separated so that the electrochemical events at one electrode do not interfere with the electrochemical events at the other electrode. The distance between electrodes 5 and 6 is about 1.2 millimeters (mm).

In the test strip shown in FIG. 1, electrically conductive track 5 would be the working electrode, and electrically conductive track 6 would be a counter electrode or reference electrode. Track 6 would be a reference electrode if made of typical reference electrode materials, such as silver/silver chloride. Track 5 is a working electrode made of palladium, and track 6 is a counter electrode that is also made of palladium and is substantially the same size as the working electrode.

Three electrode arrangements are also possible; wherein the strip includes an additional electrically conductive track located between conductive track 6 and vent hole 4. In a three electrode arrangement, conductive track 5 would be a working electrode, track 6 would be a counter electrode, and the third electrode between track 6 and vent hole 4 would be a reference electrode.

Tracks 5, 6 represent the electrodes of test strip. Tracks 5, 6 are unspooled from reels (not shown) and precut to a width of about 1.5 mm. Tracks 5, 6 are then coupled to first surface 22 of substrate 1. Tracks 5, 6 are on Upilex backing (available from Courtalds-Andus Performance Filmsare) laid down on surface 22 of substrate 1 so that the Upilex backing is adjacent to surface 22. During direct potential excitation, a reduced mediator will be principally oxidized at the working electrode while the counter-electrode primarily serves to complete the circuit.

Second substrate 7 overlaps tracks 5, 6. Second substrate 7 has a first surface 8 and a second surface 9 facing conductive tracks 5, 6. As shown in FIG. 1, second substrate 7 is formed to include first and second openings 10, 11. First opening 10 exposes portions of tracks 5, 6 for electrical connection with a meter (not shown), which measures some electrical property of a sample after the sample is mixed with reagent 12 of the test strip. Second opening 11 includes an edge that defines a perimeter of a capillary test chamber. Further, an indentation 19 that is in general alignment with indentation 2 of first substrate 1 extends from second opening 11 to an edge of second substrate 7. Second substrate 7 is coupled to first substrate 1 and tracks 5, 6 by an adhesive such as a hot melt glue. A non-limiting example of such glue is DYNAPOL S-1358 glue, available from Hüls America, Inc., 220 Davidson Street, P.O. Box 6821, Somerset, N.J. 08873.

Figure 4:
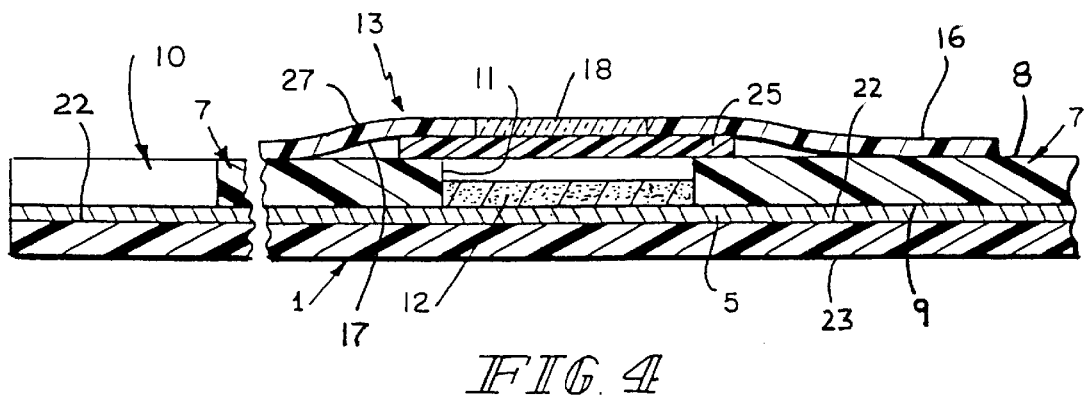
FIG. 4 is a cross-sectional view taken along lines 29—29 of FIG. 2 showing the roof, the hydrophilic film, the edges of the second opening of the second substrate, and the first insulating substrate cooperating to define a test chamber and the reagent positioned in the test chamber.

As shown in FIGS. 3 and 4, roof 13 overlays a portion of first surface 8 and second opening 11. Roof 13 includes a first surface 16 and a second surface 17 that is coupled to first surface 8 of second substrate 7. Roof 13, further includes a window 18 positioned in general alignment with second opening 11 of second substrate 7. Window 18 is dimensioned and positioned so that window 18 overlays the entire width of track 5 and at least about ten percent of the width of track 6. Additionally, a substantially opaque ink is printed on first surface 16 in pattern 27 such that window 18 remains transparent. Referring again to FIG. 1, roof 13 includes an indentation 14 and a notch 15 formed in window 18 that are shaped and positioned in general alignment with indentation 2 and notch 3 of first substrate 1. Notches 2, 15 can be defined as a generally triangular cutout from the affected edges with a length of about 0.6 to 1.3 mm and an angle at the opposite vertex of about 70–110 degrees. It is appreciated that the dimensions and configuration of notch may vary in accordance with this disclosure.

Roof 13 may be constructed of a plastic material, such as a transparent or translucent polyester foil that has a thickness of about 2 mil (0.05 mm) to 6 mil (0.15 mm) thickness. Roof 13 is constructed of Melinex 351 (polyester, containing titanium dioxide to provide opacity) which has been coated with a pressure sensitive adhesive. A non-limiting example of a suitable adhesive is 3 M 9458 acrylic, available from 3M, Identification and Converter Systems Division, 3M Center, Building 220-7W-03, St. Paul, Minn. 55144.

Additionally, roof 13 is either intrinsically hydrophilic or has been modified such that roof 13 possesses a hydrophilic surface, which is oriented toward second substrate 7. Surface 17 is modified by hydrophilic film 25, which is positioned onto the adhesive of surface 17. Hydrophilic film 25 is made hydrophilic, for example, by coating film with a detergent containing coating or a photo-crosslinked matrix of hydrophilic polymer. The film may also be modified through plasma treatment or plasma induced, covalent, modification of the surface with sulfonyl- or nitrous-groups. Hydrophilic film 25 is coated with a mixture of Vitel (The Goodyear Tire & Rubber Co., Akron, Ohio) and Rhodapex® (Rhodia, Cranbury, N.J.) surfactant at an approximate thickness of about 4 mil (0.1 mm).

The capillary test chamber is defined by second surface 17 of roof 13 having hydrophilic film 25 coupled thereto, the edges of second opening 11 of second substrate 7, and first surface 22 of substrate 1. The test chamber is positioned to expose a portion of tracks 5, 6 for application of reagent 12 to those exposed surfaces of tracks 5, 6. The length and width of this capillary test chamber are defined by the length and width of opening 11 and the height of the test chamber is defined by the thickness of second substrate 7. The test chamber is formed as a rectangle of about 3.2 mm on one side and about 6.7 mm on the other side. The degree to which tracks 5, 6 are exposed determines the surface area for each electrode. The working and counter electrodes 5, 6 each have substantially equivalent surface areas of about 5 $mm^2$. It is appreciated, however, that the degree of exposure of tracks 5, 6 may vary, as long as second opening 11 exposes at least about 10% of the width of each track 5, 6.

Reagent 12 for 3-HBA is positioned in the test chamber such that it covers working electrode 5. Reagent 12 is placed as a film of generally uniform thickness over the entire floor surface of the test chamber. Reagent 12 will then present a hydrophilic surface to the interior of the test chamber. Reagent 12 is formed to include a vent in general alignment with venting hole 4 of first substrate 1. See FIG. 3. Vents have a dimension of about 1.8 by 0.5 mm to allow air to escape from the test chamber.

The test strip incorporating reagent 12 of the present invention is manufactured by the process described in U.S. Pat. No. 5,997,817, the disclosure of which is incorporated herein by reference. It is contemplated that variations and modifications to the method of manufacture are contemplated and do not exceed the scope of the present disclosure.

Reagent 12 is formulated for the measurement of 3-HBA in a human blood sample. Reagent 12 is reactive with the sample in a manner effective to generate an electrical output signal indicative of the level of 3-HBA in the sample.

Reagent 12 comprises a mediator, enzymes, and a cofactor. Reagent 12 further comprises film forming agents as required conferring durability and providing hydrophilicity. It is appreciated that unless stated otherwise, all concentrations of components listed below refer to the concentration of a given substance in a wet-reagent prior to the deposition and drying of that reagent into the test strip.

As previously discussed, a mediator suitable for use in reagent 12 is capable of undergoing an electrochemical, reversible, oxidation-reduction reaction. The oxidized form of the mediator must be capable of receiving at least one electron from a reaction involving an enzyme, analyte (or cofactor produced from analyte reaction) and the oxidized form of the mediator. The mediator is a hexacyanoferrate (III) salt, such as, for example, potassium hexacyanoferrate (III), hereinafter "ferricyanide". Because ferricyanide is also incorporated into test strips of glucose measuring sensors, the 3-HBA test strip of the present invention beneficially will function on the same instrumentation as a corresponding glucose test strip. An example of a corresponding glucose test strip is described in U.S. Pat. No. 5,997,817, the disclosure of which is incorporated herein by reference.

The concentration range of analyte sought to be measured and the diffusive properties of the mediator through the reagent and sample govern the requisite amount of mediator in the reagent. Specifically, the amount of reduced form of mediator must be sufficient to insure that the current produced during electro-reduction is limited by the reduction of the oxidized form of the mediator at the working electrode surface. The solubility of the mediator and the impact of excessive mediator on the product stability generally govern the upper limit of the mediator concentration. The reagent for analyzing 3-HBA in accordance with the present invention includes about 112.8 mM to 56.4 mM ferricyanide, based on 329.26 mg/mmol, to measure the 3-HBA level in a sample of human whole blood from about 3.5 to 7 microliters ($\mu$L) in volume. It is appreciated that greater than 7 $\mu$L of sample may be deposited onto a test strip, but that the concentration of ferricyanide in the dissolved reagent is dependent only upon the amount of sample that enters the test chamber. It is also appreciated, however, that the concentration of ferricyanide will vary with the volume of human whole blood that enters the test chamber.

The 3-HBA test reagent of the present invention further includes enzymes that are of sufficient type and in sufficient amount to catalyze the reaction involving enzyme, analyte, and oxidized form of the mediator. One enzyme suitable for use in the reagent is operative to catalyze the oxidation of 3-HBA in the sample and a second enzyme is operative to catalyze the electrochemical oxidation of a reduced form of the cofactor. The first enzyme is a dehydrogenase and a second enzyme is diaphorase. More particularly, the first enzyme is 3-hydroxybutyrate dehydrogenase that is commercially available from Toyobo Co., Ltd. Biochemical Operations Department, Osaka, Japan and Roche Diagnostics Corporation, Roche Molecular Biochemicals, Indianapolis, Ind. 46250. The diaphorase is commercially available from Roche Diagnostics Corporation, Roche Molecular Biochemicals, Indianapolis, Ind. 46250.

For the test strip as designed for the analysis of 3-HBA, between about 0.20 and 20 million units of 3-hydroxybutyrate dehydrogenase and between about 0.1 and 10 million units of diaphorase per liter of reagent are included where the reaction is allowed to proceed for about 15 seconds at a minimum before the application of electrical potential. More preferably, the reaction is allowed to proceed for about 50 seconds at a minimum before the application of electrical potential. It is appreciated, however, that the amount of enzymes included in the reagent may vary depending upon the desired stability, the geometry of the electrodes, and the physical properties of the regent film without exceeding the scope of the present disclosure.

Additionally, the test reagent comprises a cofactor that cooperates with the enzymes and the mediator. Non-limiting examples of suitable cofactors include $NAD^+$, $NADP^+$, $NADH_2$, $NADPH_2$, and phenazine methosulfate. Preferably, the cofactor is $NAD^+$. $NAD^+$ is commercially available from Roche Diagnostics Corporation, Roche Molecular Biochemicals, Indianapolis, Ind. 46250. The reagent for analyzing 3-HBA in accordance with the present invention includes about 21.1 $\mu$M to 43 $\mu$M $NAD^+$, based on 663.44 g/mol, to measure the 3-HBA level in a sample of human whole blood from about 3.5 to 7 microliters ($\mu$L) in volume. It is appreciated that greater than 7 $\mu$L of sample may be deposited onto test strip, but that the concentration of $NAD^+$ in the dissolved reagent is dependent only upon the amount of sample that enters the test chamber. It is also appreciated, however, that the concentration of $NAD^+$ will vary with the volume of human whole blood that enters the test chamber.

To improve the solubilization of the mediator, various "filler" substances can be included in the reagent. A filler is defined here as an insoluble particulate of microscopic size that is evenly dispersed through the regent matrix during the compounding of reagent. The preferred filler is a metal oxide that does not accept or donate electrons at the applied potential or relative to the potential of the mediator or mediators. Reagent 12 includes a filler such as titanium dioxide present in an amount from about 0.2 to 2.0% (wet mass:wet mass) and is preferably about 0.22% (wet mass: wet mass).

When fillers are used, substances such as polymers are generally included in the reagent to raise the viscosity of reagent 12. Reagent 12 includes the polymer Natrosol 250K (Hydroxyethyl Cellulose, available from Aqualon Oil Field Chemicals, Houston, Tex.). The amount of Natrosol 250K may vary from about 0.05 to 0.5% (wet mass:wet mass) and the preferred concentration is about 0.19% (wet mass:wet mass). It is appreciated that a variety of commercially available viscositiers may be use in accordance with the present disclosure.

Hydrophilic polymers can confer both durability and hydrophilicity to the reagent. Some non-limiting examples of acceptable polymers are polyethylene glycol/polyethylene oxide, polyvinyl-alcohol, polyvinyl-pyrrholidine, polystyrene sulfonate, polyvinyl-acetate and microemulsions of vinyl-acetate. Polyethylene oxide (Union Carbide Corporation, Danbury, Conn.) of about 100 to 900 kilodalton mean molecular weight is used at concentrations of about 0.2% to 2% (wet mass:wet mass). Reagent 12 includes polyethylene oxide of about 300 kilodalton mean molecular weight at about 0.59% (wet mass:wet mass).

Surfactant is generally included in the reagent to control (decrease) the surface tension. Non-limiting examples of acceptable detergents are DONS (sodium dioctyl sulfosuccinate), branched-nonyl phenoxypoly (ethyleneoxy) ethanol (available from Rhone-Poulenc, Collegeville, Pa. as Igepal CO-630 or from Roche Diagnostics, Biochemicals, Indianapolis, Ind. as Triton X-100). The quantity and type of detergent in the reagent will be sufficient to reduce the surface tension to between about 20 and 70 dynes/cm. Where the sample is to be blood, the undesired lysis of cells should be avoided by restricting the overall concentration of the detergent to levels below about 0.3%

(dependent upon the type of detergent). For the test strip designed to assay 3-HBA using glucose dehydrogenase, Triton X-100 is present at concentrations no higher than about 0.05% (wet mass:wet mass), with about 0.035% (wet mass:wet mass) being preferred.

Reagent 12 may include a buffer. The buffer is of sufficient type and in sufficient amount to provide and maintain a pH where the enzyme stability and activity are co-optimal. The activity of the enzyme refers to the ability of the enzyme to catalyze the reaction between analyte and mediator or analyte and analyte derivative for multi-enzyme reagents. The stability of the enzyme(s) refers to the conservation of that activity over time and when the reagent is exposed to various forms of stress, such as heat and humidity. Additionally, the buffer must not have an oxidation potential lower than that of the reduced mediator. Non-limiting examples of suitable buffers include pyrophosphate salts where the pH is between about 7.8 and 9.0 with about 8.7 being most preferable. Non-limiting examples of suitable pyrophosphate salts include disodium pyrophosphate and tetrasoduim pyrophosphate. If the optimal pH for the enzyme activity is significantly different than that of the sample, then the buffer should be of a concentration sufficient to bring the final pH of the rehydrated reagent plus sample to the desired level. The concentration of buffer generally used is between about 50 and 200 mM in the reagent. The preferred concentration is about 53.6 mM.

The reagent may also contain substances that stabilize the various components. Acceptable stabilizers for the enzymes in combination with a cofactor in the reagent of the present invention are flavin mononucleotide, adenosine diphosphate, magnesium ions, lactose, trehalose, and raffinose. Reagent 12 includes a stabilizer such as raffinose in a concentration of about 0.5 to 5% (wet mass:wet mass), with about 0.68% (wet mass:wet mass) being preferred.

The dried reagent film thickness will be such that, in combination with the inherent properties of the chemistry, the sensitivity of the system to interference from hematocrit variation is mitigated. The film thickness (as gauged by the ratio of wet reagent dispense volume to the surface area dispensed onto) is such that about 10 µL of reagent is dispensed into an area of about 22.5 millimeters square. The reagent described below, through the use of the principal polymer, polyethylene oxide, and in combination with the film thickness with result in the test strip possessing a reduced sensitivity to hematocrit variation.

When a sample containing the analyte 3-HBA is added to the reagent, the analyte is oxidized and the oxidized form of the cofactor is reduced. This cofactor then interacts with a second enzyme and the oxidized mediator is reduced. The reaction is allowed to reach a point in time at which the utilization of analyte and oxidized mediator has reached a point where additional time is not necessary for the accurate determination of analyte concentration. During this incubation time, it may be necessary to place a small magnitude alternating potential across the electrodes to determine the magnitude of interference due to shifts in impedance. See for example, U.S. patent application Ser. No. 08/996,280, filed Dec. 22, 1997, to Beaty et al., the disclosure of which is incorporated herein by reference.

The oxidization of the analyte and reduction of the oxidized form of the cofactor are permitted to go to completion. The term completion, as used throughout the specification and claims, is defined as a sufficient reaction involving analyte, cofactor, and enzyme to form one or more reduced reaction products and a sufficient reaction involving the one or more reduced reaction products, enzyme, and mediator to correlate the analyte concentration to diffusion limited current generated by oxidation of the mediator at the surface of the working electrode.

After the reactions are complete, a potential difference is applied between a working and counter electrode to cause diffusion limited electro-oxidation of the reduced form of the mediator at the working electrode surface. A current measuring meter measures the diffusion limited current generated by the oxidation of the reduced form of the mediator at the working electrode surface. The measured current may be accurately correlated to the concentration of 3-HBA in the sample when the following requirements are satisfied:

1. The rate of oxidation of the reduced form of the mediator is governed by the rate of diffusion of the reduced form of the mediator to the surface of the working electrode.
2. The current produced is limited by the oxidation of reduced form of the mediator at the surface of the working electrode.

The test strip of the present invention satisfies the above requirements by employing reagent 12 that includes a readily reversible mediator and by supplying reagent with the oxidized form of the mediator in an amount sufficient to insure that the current produced during diffusion limited electro-oxidation is limited by the oxidation of the reduced form of the mediator at the working electrode surface. For current produced during electro-oxidation to be limited by the oxidation of the reduced form of the mediator at the surface of the working electrode, the amount of the oxidized form of the mediator at the surface of the counter electrode must always exceed the amount of the reduced form at the surface of the working electrode.

Thus, the test strip and method utilizing the reagent of the present invention provide the user with a convenient and easy means for determining the levels of 3-HBA in the blood. Test strip and method essentially eliminate the disadvantages to the user having to purchase or use separate instrumentation for testing for blood glucose and for 3-HBA.

A protocol for the preparation of 1 liter of a 3-HBA determining reagent utilizing the enzymes hydroxybutyrate dehydrogenase and diaphorase and the mediator ferricyanide is shown below.

Step 1: A solution of Natrosol (250K) in deionized water is prepared by adding 1.90 g of Natrosol K to the surface of 430 g of deionized water while mixing with a rotary mixer and impeller at a speed of no less than about 400 revolutions per minute (rpm) for a period of no less than about 30 minutes.

Step 2: To the solution from Step 1, 6.1 g polyethylene oxide (300 kilodalton mean molecular weight) (Union Carbide 750NF) is dispersed by gradually adding the powder over the surface of the solution while mixing at a speed of no less than about 400 rpm for a period of no less than about 60 minutes.

Step 3: To the mixture from Step 2, 6.8 g of raffinose is dispersed by gradually adding the power over the surface of the solution while mixing at a speed of no less than 400 rpm for a period of not less than 10 minutes.

Step 4: The mixture from Step 3 is buffered by adding 58.8 g of disodium pyrophosphate (anhydrous) and 73.1 g of tetrasodium pyrophosphate (anhydrous) while mixing at a speed of 400 rpm of a period of no less than 20 minutes. The final pH of 8.7 is checked. This sub-build is referred to from this point forward as the "Polymer Matrix".

Step 5: A suspension of titanium dioxide is prepared by dispensing 2.3 g of titanium dioxide powder over 377.8 g of deionized water while mixing with a rotary mixer and impeller at a speed of no less than 600 rpm for no less than 20 minutes. This sub-build is referred to from this point forward as the "Filler-Suspension".

Step 6: The Filler-Suspension from Step 5 was combined with the Polymer Matrix of Step 4. This combination is preformed by filtering the Filler Suspension through a coarse (200 micron) mesh to remove any large, undispersed, particles of titanium dioxide prior to or during the combining step.

Step 7: Next, 13.3 g of potassium ferricyanide is added to the reagent from Step 6. The reagent is allowed to mix at no less than 500 rpm for not less than 20 minutes or until ready for final reagent assembly (Step 13). This matrix is referred to from this point forward as the "Reagent Base".

Step 8: A separate solution is prepared by dispersing 200,000 units of β-Hydroxybutyrate dehydrogenase enzyme into 100 g of deionized water while stirring at a rate no less than 200 rpm using a stir plate and magnetic stirrer.

Step 9: To the solution from Step 8, 200,000 units of Diaphorase enzyme are added and allowed to mix for 10 minutes. This solution is referred to as the "Enzyme Solution" hereafter. The resulting Solution is refrigerated at about 4° C. to 10° C. until ready to incorporate into the final reagent (Step 13).

Step 10: A separate solution is prepared by dissolving 96 mg of Magnesium chloride-hexahydrate into 50 g of deionized water.

Step 11: To the solution from Step 10, 200 mg of cofactor $NAD^+$ are dissolved while mixing at 200 rpm for 5 minutes.

Step 12: To the solution from Step 11, 145 mg of flavin mononucleotide are dissolved while mixing at 200 rpm for 5 minutes. This is referred to as the "Cofactor Solution" hereafter. The Cofactor Solution is refrigerated at about 4° C. to 10° C. until ready for final incorporation into the reagent (Step 13).

Step 13: The final reagent was assembled by adding the Enzyme Solution from Step 9 and Cofactor Solution from Step 12 to the Reagent Base from Step 7. The final reagent was stirred at a reduced speed of 400 rpm for no less than 15 minutes.

Step 14: The final reagent is completed with the addition of 0.35 g of Triton X-100 and stirring at 400 rpm for no less than 15 minutes prior to dispense.

A test strip of the present invention is manufactured by the process described in U.S. Pat. No. 5,997,817, the disclosure of which is incorporated herein by reference. To the test strip, for 3-HBA determination, 10 μL of reagent made by the above-described protocol was added to the electrode-bearing surface of the test-chamber. The amount of reagent may vary from about 3 to 10 μL, with the preferred dispense of about 10 μL. This amount of reagent will substantially cover the surface areas of the electrodes. The resulting reagent film will contain sufficient ferricyanide and enzymes (β-hydroxybutyrate dehydrogenase and Diaphorase) to catalyze the oxidation of 3-HBA (from a sample of human whole blood) and the reduction of ferricyanide to allow the accurate and precise determination of 3-HBA concentration after an initial incubation (prior to the application of potential) within about 60 seconds.

To ensure a uniformly distributed, homogeneous reagent layer on drying, the electrode bearing surface of the test-chamber, the surface is treated with a 150 Watt corona arc, grapped at 1/40,000 inch immediately prior to the application of the reagent. This application is made with the material passing through a processing line of about 6.5 meters per minute. This treatment raises the surface energy of the target area to encourage the spreading of the wet reagent prior to drying. The corona arc is applied about 5 minutes at a maximum, and more preferably less than about 45 seconds, prior to dispensing of the reagent onto the material. Subsequent to the application of the arc, and prior to dispensing the reagent, the corona treatment is reduced on the surface of the spacer layer where reagent is not desired.

This corona dissipation is accomplished by the application of a film of deionized water such that the water comes into contact with the surface of the spacer layer, but will not come into contact with the electrode bearing surface of the base layer. The film of water which is placed onto the surface of the spacer layer is sufficiently thin to be dried by either infrared or mechanical convection method prior to the material reaching the are of reagent dispense.

Reagent is then dried with heating at about 70° C. Drying removes at least about 98% of the water content of the reagent. Remaining water is reduced to trace levels during subsequent desiccation in a final packaging device. The resulting, dry reagent film would contain between 1 and 5 thousand units of activity per enzyme per gram.

A non-limiting example of components that are used to form 100 g of reagent of the present invention are listed below in Table 1.

TABLE 1

| wet mass (g) | % | dry mass (g) | mass/g dry mass (mg) | % | dry mass/ sensor (mg) | component |
|---|---|---|---|---|---|---|
| 95.78 | | | | | | DI water |
| 0.61 | 0.60 | 0.61 | 120.8 | 12.1 | 0.06010 | PEO 750N |
| 0.19 | 0.19 | 0.19 | 37.6 | 3.8 | 0.01872 | Natrosol 250K |
| 0.23 | 0.23 | 0.23 | 45.6 | 4.6 | 0.02266 | Titanium Dioxide |
| 0.58 | 0.57 | 0.58 | 114.9 | 11.5 | 0.05715 | Di Sodium Pyrophosphate |
| 0.73 | 0.72 | 0.73 | 144.8 | 14.5 | 0.07202 | Tetra Sodium Pyrophosphate |
| 1.33 | 1.31 | 1.33 | 264.1 | 26.4 | 0.03137 | Potassium ferricyanide |
| 0.68 | 0.67 | 0.68 | 134.7 | 13.5 | 0.06700 | Raffinose |
| 0.0200 | 0.0197 | 0.0200 | 4.0 | 0.4 | 0.00197 | NAD+ |
| 0.0145 | 0.0143 | 0.0145 | 2.9 | 0.3 | 0.00173 | Flavin Mononucleotide |

TABLE 1-continued

| wet mass (g) | % | dry mass (g) | mass/g dry mass (mg) | % | dry mass/ sensor (mg) | component |
|---|---|---|---|---|---|---|
| 0.0096 | 0.0095 | 0.0096 | 1.9 | 0.2 | 0.00095 | Magnesium Chloride |
| 0.05 | 0.05 | 0.05 | 909 | 1.0 | 0.00493 | Triton X-100 |
| 0.3 | 0.92 | 0.47 | 92.4 | 9.2 | 0.09196 | β-Hydroxybutyrate dehydrogenase (given 2 U/mg) |
| 0.33 | 0.33 | 0.13 | 26.4 | 2.6 | 0.03284 | Diaphorase enzyme (*B. stearothermicus*) (given 32 U/mg) |
| 101.50 | | 5.05 | | 1000.0 | | TOTAL |

The discrete test strips are used in conjunction with the following:
1. a power source in electrical connection with the working and counter electrodes and capable of supplying an electrical potential difference between the working and counter electrodes sufficient to cause diffusion limited electro-oxidation of the reduced form of the mediator at the surface of the working electrode; and
2. a meter in electrical connection with the working and counter electrodes and capable of measuring the diffusion limited current produced by oxidation of the reduced form of the mediator with the above-stated electrical potential difference is applied.

The meter will normally be adapted to apply an algorithm, as discussed below, to the current measurement, whereby an analyte concentration is provided and visually displayed. Such a power source, meter, and biosensor system are the subject of U.S. Pat. Nos. 4,963,814; 4,999,632; 4,999,582; and 5,243,516, and U.S. patent application Ser. No. 08/996,280, filed Dec. 22, 1997 to Beaty et al., the disclosures of which are incorporated herein by reference.

The test strip including the reagent of the present invention may be used to determine the concentration of an analyte in a fluid sample by performing the following steps:
a. contacting the fluid sample with the reagent that substantially covers substantially equal surface areas of working and counter electrodes;
b. allowing the reaction between the analyte and the oxidized form of the mediator to go to completion and measuring background impedance by using a low (57 mV amplitude), medium to high frequency (100 Hz+) alternating potential for internal calibration during the incubation period;
c. subsequently applying a direct potential difference between the electrodes sufficient to cause diffusion limited electro-oxidation of the reduced form of the mediator at the surface of the working electrode;
d. thereafter measuring the resulting diffusion limited current; and
e. correlating the current measurement to the concentration of analyte in the fluid.

Many 3-HBA-containing fluids may be analyzed. For example, 3-HBA in human body fluids such as whole blood, blood serum, urine, and cerebrospinal fluid may be measured. Also, 3-HBA found in food products, fermentation products, and in environmental substances, which potentially contain environmental contaminants, may be measured.

When measuring analytes found in human body fluids, especially whole blood, the potential difference applied between the electrodes should be no more than about 500 millivolts. When a potential difference above about 500 millivolts is applied between the electrodes, oxidation of the working electrode surface (for palladium) and of some blood components can become intolerable, thereby preventing an accurate and precise correlation of current to analyte concentration. For an assay of 3-HBA in a whole blood sample, wherein the oxidized form of the mediator is ferricyanide, a potential difference from about 150 millivolts to 500 millivolts may be applied between the electrodes to achieve diffusion limited electro-oxidation of the reduced form of the ferricyanide at the surface of the working electrode. About 300 millivolts potential difference is applied between the electrodes.

Current generated from the oxidation of the reduced form of the mediator may be measured at any time from about 0.5 seconds to 30 seconds after the potential difference is applied between the electrodes. At less than about 0.5 seconds, diffusion limited current has not been achieved. After about 30 seconds, convection becomes significant thereby interfering with the measurement of a diffusion-limited current. The current measured during the assay of an analyte from a fluid sample may be correlated to concentration of the analyte in the sample by application of an algorithm by the current measuring meter. The algorithm may be a simple one, as illustrated by the following example:

$$[\text{Analyte}] = Ci7.5 + d$$

wherein [Analyte] represents the concentration of the 3-HBA analyte in the sample (see FIG. 5), i is the current (in microamps) measured at 9.0 seconds after application of the potential difference applied between the electrodes, C is the slope of the line: e.g. 0.483 for Trial A, and 0.528 for Trial B, and d is the axis intercept: e.g. −2.82 for Trial A and −1.23 for Trial B. Therefore, the concentrations of 3-HBA for Trials A and B were d determined as follows:

Trial A: [3-HBA]=Current×0.483−2.82

Trial B: [3-HBA]=Current×0.528−1.23

Figure 5:
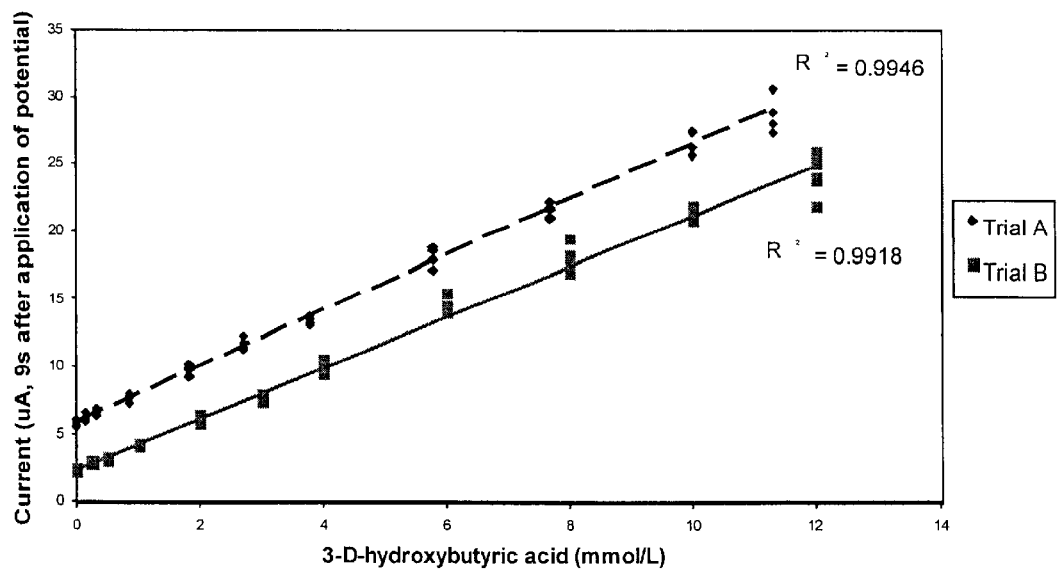
FIG. 5 is a graph showing calibration curves for different lots of test strips.

By making measurements with known concentrations of 3-HBA analyte, calibration curves may be constructed, as shown in FIG. 5. This calibration will be stored in the Read Only Memory (ROM) key of the meter and will be applicable to a particular lot of biosensors.

In the method for analysis of 3-HBA from a sample of whole human blood, 5 μL of whole blood is added to the above-described reagent 12. The reaction is allowed to proceed to a stable point, forming a stable concentration of ferrocyanide. During this time, 57 mV amplitude, 2 kHz frequency alternating current is applied to determine background impedance. About fifty seconds after addition of the whole blood sample, a direct potential difference of about 300 millivolts is applied between the electrodes, thereby oxidizing ferrocyanide to ferricyanide at the surface of the working electrode. Current measurements are made at 0.5 second intervals from 1 second to 9.0 seconds after the potential difference is applied between the electrodes. These current measurements are correlated to the concentration of 3-HBA in the blood sample.

In this example of measuring 3-HBA from a blood sample, current measurements are made at different times (from 1 second to 7.5 seconds after application of the potential difference), rather than at a single fixed time (as previously described), and the resulting algorithm is represented by the following equation:

$$[3\text{-HBA}] = C1\ i1 + C2\ i2 + C3\ i3 + \ldots Cn\ in + d$$

wherein i1 is the current measured at the first measurement time (1 second after application of the 300 millivolt potential difference), i2 is the current measured at the second measurement time (1.5 seconds after application of the 300 millivolt potential difference), i3 is the current measured at the third measurement time (2 seconds after application of the 300 millivolt potential difference), in is the current measured at the nth measurement time (in this example, at the fourteenth measuring time or 7.5 seconds after application of the 300 millivolt potential difference), C1, C2, C3, and Cn are coefficients derived from a multivariate regression analysis technique, such as Principle Components Analysis or Partial Least Squares, and d is the regression intercept (in 3-HBA concentration units).

Alternatively, the concentration of 3-HBA in the sample being measured may be determined by integrating the curve generated by plotting current, i, versus measurement time over some time interval (for example, from 1 second to 7.5 seconds after application of the 300 millivolt potential difference), thereby obtaining the total charge transferred during the measurement period. The total charge transferred is directly proportional to the concentration of the 3-HBA in the sample being measured.

Further, the 3-HBA concentration measurement may be corrected for differences between environmental temperature at the time of actual measurement and the environmental temperature at the time calibration. For example, if the calibration curve for 3-HBA was constructed at the environmental temperature of 23° C., the 3-HBA measurement is corrected by using the following equation:

$$[3\text{-HBA}]\text{corrected} = [3\text{-HBA}]\text{measured} \times (1 - K(T - 23° \text{ C.})$$

wherein T is the environmental temperature (in ° C.) at the time of the sample measurement and K is a constant derived from the following regression equation:

$$Y = K(T - 23),$$

wherein Y=[3-HBA] measured at 23° C.−[3-HBA] measured at T.

In order to calculate the value of K, each of the multiplicity of 3-HBA concentrations is measured by the meter at various temperatures, T and at 23° C. (the base case). Next, a linear regression of Y on T−23 is performed. The value of K is the slope of this regression.

The 3-HBA concentration of a sample may be measured by the present inventive method utilizing the present inventive test strip. Further, when a sample of human whole blood is measured, error due to hematocrit effect is insignificant in the range of about 30 to 55% hematocrit.

The present invention has been illustrated by analytes that are oxidized and mediators that are reduced in the presence of a catalytic amount of enzyme. However, the present invention, reagents and methods may be used to measure the concentration of an analyte in a fluid sample, wherein the analyte is reduced and the reduced form of a mediator is oxidized in the presence of a catalytic amount of an enzyme (e.g., a reductase). After the reaction involving analyte, enzyme, and reduced form of the mediator reaches completion, a potential difference is applied between the electrodes. The amount of reduced form of the mediator at the counter electrode (in this case an anode rather than a cathode) and the applied potential difference must be sufficient to cause diffusion limited electroreduction of the oxidized form of the mediator at the surface of the working electrode (in this case a cathode rather than an anode). The diffusion-limited current generated by reduction of the oxidized form of the mediator at the working electrode surface is correlated to the concentration of analyte in the sample being analyzed.

Although the invention has been described in detail with reference to certain preferred embodiments, it is appreciated that variations and modifications exist within the scope and spirit of the present invention as described and defined in the following claims.

What is claimed is:

1. A single-use disposable test strip apparatus for detecting 3-hydroxybutyric acid in a liquid sample, the apparatus comprising:
    a substrate,
    at least one electrode positioned on the substrate, and
    a single-use reagent in communication with the at least one electrode, the reagent being formed to dissolve in the liquid sample and to generate an electrical output signal indicative of the level of 3-hydroxybutyric acid in the sample, said reagent comprising a hexacyanoferrate (III) salt, a catalytic amount of a first enzyme operative to catalyze the oxidation of 3-hydroxybutyric acid in the sample, a cofactor corresponding to said first enzyme, and a catalytic amount of a second enzyme operative to catalyze the electrochemical oxidation of a reduced form of the cofactor.

2. The apparatus of claim 1, wherein the first enzyme is a dehydrogenase.

3. The apparatus of claim 2, wherein the first enzyme is hydroxybutyrate dehydrogenase.

4. The apparatus of claim 3, wherein the second enzyme is diaphorase.

5. The apparatus of claim 4, wherein the cofactor is selected from the group consisting of $NAD^+$, $NADP^+$, $NADH_2$, and $NADPH_2$.

6. The apparatus of claim 3, wherein the cofactor is selected from the group consisting of $NAD^+$, $NADP^+$, $NADH_2$, and $NADPH_2$.

7. The apparatus of claim 2 wherein the second enzyme is a diaphorase.

8. The apparatus of claim 7, wherein the cofactor is selected from the group consisting of $NAD^+$, $NADP^+$, $NADH_2$, and $NADPH_2$.

9. The apparatus of claim 2, wherein the cofactor is selected from the group consisting of $NAD^+$, $NADP^+$, $NADH_2$, and $NADPH_2$.

10. The apparatus of claim 1, wherein the second enzyme is diaphorase.

11. The apparatus of claim 10, wherein the cofactor is selected from the group consisting of $NAD^+$, $NADP^+$, $NADH_2$, and $NADPH_2$.

12. The apparatus of claim 1, wherein the cofactor is selected from the group consisting of $NAD^+$, $NADP^+$, $NADH_2$, and $NADPH_2$.

13. The apparatus of claim 12, wherein the cofactor is $NAD^+$.

14. The apparatus of claim 1, wherein the ferricyanide salt is potassium hexacyanoferrate (III).

15. A single-use disposable test strip apparatus for detecting 3-hydroxybutyric acid in a liquid sample, the apparatus comprising:
   a substrate,
   at least one electrode positioned on the substrate, and
   a single-use reagent in communication with the at least one electrode, the reagent being formed to dissolve in the liquid sample and being reactive with the sample in a manner effective to generate an electrical output signal indicative of the level of 3-hydroxybutyric acid in the sample, said reagent comprising a hexacyanoferrate (III) salt, a catalytic amount of a first enzyme operative to catalyze the oxidation of 3-hydroxybutyric acid in the sample, a cofactor corresponding to said first enzyme, and a catalytic amount of a second enzyme operative to catalyze the electrochemical oxidation of a reduced form of the cofactor, wherein the reagent further comprises a filler.

16. The apparatus of claim 15, wherein the filler is a metal oxide.

17. A single-use disposable test strip apparatus for detecting 3-hydroxybutyric acid in a liquid sample, the apparatus comprising:
   a substrate,
   at least one electrode positioned on the substrate, and
   a single-use reagent in communication with the at least one electrode, the reagent being formed to dissolve in the liquid sample and being reactive with the sample in a manner effective to generate an electrical output signal indicative of the level of 3-hydroxybutyric acid in the sample, said reagent comprising a hexacyanoferrate (III) salt, a catalytic amount of a first enzyme operative to catalyze the oxidation of 3-hydroxybutyric acid in the sample, a cofactor corresponding to said first enzyme, a catalytic amount of a second enzyme operative to catalyze the electrochemical oxidation of a reduced form of the cofactor, and a polymer selected from the group consisting of polyethylene glycol/polyethylene oxide, polyvinyl-alcohol, polyvinyl-pyrrholidine, polystyrene sulfonate, polyvinyl-acetate and microemulsions of vinyl-acetate.

18. A single-use disposable test strip apparatus for detecting 3-hydroxybutyric acid in a liquid sample, the apparatus comprising:
   a substrate,
   at least one electrode positioned on the substrate, and
   a single-use reagent in communication with the at least one electrode, the reagent being formed to dissolve in the liquid sample and being reactive with the sample in a manner effective to generate an electrical output signal indicative of the level of 3-hydroxybutyric acid in the sample, said reagent comprising a hexacyanoferrate (III) salt, a catalytic amount of a first enzyme operative to catalyze the oxidation of 3-hydroxybutyric acid in the sample, a cofactor corresponding to said first enzyme, a catalytic amount of a second enzyme operative to catalyze the electrochemical oxidation of a reduced form of the cofactor, and a surfactant.

19. The apparatus of claim 18, wherein the surfactant is selected from the group consisting of sodium dioctyl sulfosuccinate and branched-nonyl phenoxypoly (ethylene-oxy) ethanol.

20. A single-use disposable test strip apparatus for detecting 3-hydroxybutyric acid in a liquid sample, the apparatus comprising:
   a substrate,
   at least one electrode positioned on the substrate, and
   a single-use reagent in communication with the at least one electrode, the reagent being formed to dissolve in the liquid sample and being reactive with the sample in a manner effective to generate an electrical output signal indicative of the level of 3-hydroxybutyric acid in the sample, said reagent comprising a hexacyanoferrate (III) salt, a catalytic amount of a first enzyme operative to catalyze the oxidation of 3-hydroxybutyric acid in the sample, a cofactor corresponding to said first enzyme, a catalytic amount of a second enzyme operative to catalyze the electrochemical oxidation of a reduced form of the cofactor, and an inorganic buffer.

21. The apparatus of claim 20, wherein the buffer is a pyrophosphate salt.

22. A single-use disposable test strip apparatus for detecting 3-hydroxybutyric acid in a liquid sample, the apparatus comprising:
   a substrate,
   at least one electrode positioned on the substrate, and
   a single-use reagent in communication with the at least one electrode, the reagent being formed to dissolve in the liquid sample and being reactive with the sample in a manner effective to generate an electrical output signal indicative of the level of 3-hydroxybutyric acid in the sample, said reagent comprising a hexacyanoferrate (III) salt, a catalytic amount of a first enzyme operative to catalyze the oxidation of 3-hydroxybutyric acid in the sample, a cofactor corresponding to said first enzyme, a catalytic amount of a second enzyme operative to catalyze the electrochemical oxidation of a reduced form of the cofactor, and stabilizers selected from the group consisting of flavin mononucleotide, adenosine diphosphate, magnesium ions, lactose, and raffinose.

23. A method for determining information indicative of the level of 3-hydroxybutyric acid in a liquid sample, the method comprising the steps of:
   reacting the sample with a single-use reagent formed to dissolve in the liquid sample, the reagent comprising a ferricyanide salt, a catalytic amount of a first enzyme operative to catalyze the oxidation of 3-hydroxybutyric acid in the sample, a cofactor corresponding to said first enzyme, and a catalytic amount of a second enzyme operative to catalyze the oxidization of the cofactor and the reduction of the ferricyanide,
   generating an electrical output from the dissolved reagent indicative of the level of 3-hydroxybutyric acid in the sample,
   measuring the electrical output; and
   determining the level of 3-hydroxybutyric acid in the sample using information comprising the measured electrical output.

24. The method of claim 23, wherein the generating step includes applying an electrical potential to the reagent.

25. The method of claim 24, wherein the electrical potential is applied upon completion of the reaction of the sample and the reagent.

26. The method of claim 25, wherein the reaction is completed in about 60 seconds.

27. A method for determining information indicative off the level of 3-hydroxybutyric acid in a liquid sample, the method comprising the steps of:

providing a single-use disposable sensor including a working and counter electrodes and a reagent in communication with the electrodes, the reagent being formed to dissolve in the liquid sample and comprising a ferricyanide salt, a catalytic amount of a first enzyme operative to catalyze the oxidation of 3-hydroxybutyric acid in the fluid sample, a cofactor corresponding to said first enzyme, and a catalytic amount of a second enzyme operative to catalyze the oxidization of the cofactor and the reduction of the ferricyanide, contacting the reagent with the liquid sample, and applying a direct potential difference between the electrodes sufficient to generate an electrical output from the dissolved reagent indicative of the level of 3-hydroxybutyric acid in the fluid sample.

28. The method of claim 27, wherein the applying step occurs at least about 15 seconds after the contacting step.

29. The method of claim 28, wherein the applying step occurs about 50 seconds after the contacting step.

30. The method of claim 27, further comprising the step of measuring background impedance of the analyte and reagent.

* * * * *